United States Patent
Gilliam

(10) Patent No.: US 11,231,324 B2
(45) Date of Patent: Jan. 25, 2022

(54) REAL-TIME MONITORING OF WINE FERMENTATION PROPERTIES USING RAMAN SPECTROSCOPY

(71) Applicant: Kaiser Optical Systems Inc., Ann Arbor, MI (US)

(72) Inventor: Sean J. Gilliam, Plymouth, MI (US)

(73) Assignee: Kaiser Optical Systems Inc., Ann Arbor, MI (US)

( * ) Notice: Subject to any disclaimer, the term of this patent is extended or adjusted under 35 U.S.C. 154(b) by 0 days.

(21) Appl. No.: 17/174,949

(22) Filed: Feb. 12, 2021

(65) Prior Publication Data

US 2021/0255040 A1    Aug. 19, 2021

Related U.S. Application Data

(60) Provisional application No. 62/975,872, filed on Feb. 13, 2020.

(51) Int. Cl.
| | | |
|---|---|---|
| *G01J 3/44* | (2006.01) | |
| *G01N 21/65* | (2006.01) | |
| *G01N 21/84* | (2006.01) | |

(52) U.S. Cl.
CPC ............ *G01J 3/4412* (2013.01); *G01N 21/65* (2013.01); *G01N 2021/8466* (2013.01)

(58) Field of Classification Search
CPC .. G01J 3/44; G01J 3/4412; G01J 3/02; G01N 21/65; G01N 21/64; G01N 21/31; G01N 21/49; A61B 5/0075
See application file for complete search history.

(56) References Cited

U.S. PATENT DOCUMENTS

| | | | |
|---|---|---|---|
| 10,563,163 B2 | 2/2020 | Berry et al. | |
| 2016/0299060 A1* | 10/2016 | Hokanson | G01N 15/1468 |

(Continued)

FOREIGN PATENT DOCUMENTS

| | | |
|---|---|---|
| CN | 105548138 B | 4/2018 |

OTHER PUBLICATIONS

Wu, Zhengzong, Xu, Enbo, Long, Jie, Wang, Fang, Xu, Xueming, Jin, Zhengyu, Jiao, Aiquan, Measurement of fermentation parameters of Chinese rice wine using Raman spectroscopy combined with linear and non-linear regression methods, Elsevier, Food Control 56 (2015) 95-102.

(Continued)

*Primary Examiner* — Abdullahi Nur
(74) *Attorney, Agent, or Firm* — Christopher R. Powers; Endress+Hauser (USA) Holding Inc.

(57) ABSTRACT

A method of characterizing and monitoring a fermentation process includes acquiring online Raman spectra of a fermentation process within a fermenter vessel at different times during the fermentation process to generate a training data set; acquiring physical samples from fermentation process near in time to the acquired Raman spectra; performing offline measurements of the target analyte properties and/or compositions using an assay measurement technique; generating a correlative model of the target analyte such that spectral changes in the training data set correlate with the offline measurements of the target analyte properties and/or compositions; acquiring online Raman spectra of a subsequent run of the fermentation process within the fermenter vessel at different times during the run to generate a process data set; and applying the correlative model to the process data set to qualitatively and/or quantitatively predict a value of a property and/or composition of the target analyte.

19 Claims, 6 Drawing Sheets

(56) References Cited

U.S. PATENT DOCUMENTS

2017/0191947 A1     7/2017   Gilliam
2019/0137338 A1     5/2019   Webster et al.

OTHER PUBLICATIONS

Wang, Qiaoyun, Li, Zhigang, Ma, Zhenhe and Si, Guangyuan, Quantitative Analysis of Multiple Components in Wine Fermentation using Raman Spectroscopy, Advanced Journal of Food Science and Technology 9(1): 13-18, 2015.

Martin, Coralie, Bruneel, Jean-Luc, Guyon, Franois, Médina, Jourdes, Michael, Teissedre, Pierre-Louis, Guillaume, François, Raman spectroscopy of white wines, Elsevier, Food Chemistry 181 (2015) 235-240.

Gallego, Álvaro, Guesalaga, Andrés R., Bordeu, Edmundo and González, Álvaro, Rapid Measurement of Phenolics Compounds in Red Wine Using Raman Spectroscopy, IEEE Transactions on Instrumentation and Measurement, vol. 60, No. 2, Feb. 2011, 507-512.

Wang, Qiaoyun, Li, Zhigang, Ma, Zhenhe and Liang, Liqin, Real time monitoring of multiple components in wine fermentation using an on-line auto-calibration Raman spectroscopy, Elsevier, Sensors and Actuators B 202 (2014) 426-432.

Cozzolino, Daniel, Sample presentation, sources of error and future perspectives on the application of vibrational spectroscopy in the wine industry, Society of Chemical Industry, J Sci Food Agric 2015; 95: 861-868.

\* cited by examiner

REAL-TIME MONITORING OF WINE FERMENTATION PROPERTIES USING RAMAN SPECTROSCOPY

CROSS-REFERENCE TO RELATED APPLICATION

The present application is related to and claims the priority benefit of U.S. Provisional Patent Application No. 62/975,872, filed on Feb. 13, 2020, the entire contents of which are incorporated herein by reference.

TECHNICAL FIELD

The present disclosure generally relates to Raman spectroscopy and, in particular, to a method applying Raman spectroscopy to wine fermentation processes in a production setting.

BACKGROUND

Raman spectroscopy is a technique used to measure the wavelength and intensity of inelastically scattered radiation (e.g., light) from a sample, thereby revealing chemical and structural composition of the sample. Raman spectroscopy is based on the principle that monochromatic excitation light will be reflected, absorbed, or scattered as a function of the particular molecule (e.g., protein, peptide, carbohydrate, cytokine, salt, etc.) that receives the incident radiation. Most of the energy is scattered at the same wavelength of the excitation light, referred to as elastic or Rayleigh scattering. A much, much smaller amount (e.g., ~0.001%) is scattered at different wavelengths, called inelastic or Raman scattering, the wavelength of which are dependent on the molecular composition of the region sampled. In Raman spectroscopic analysis (interchangeably, Raman analysis and Raman spectroscopy), these wavelength shifts are captured in Raman spectra comprising the Raman scattered light (i.e., the Raman signal), which are analyzed to determine sample properties, including both chemical and physical properties.

Generally, practical implementations of Raman analysis include data processing and modeling of the Raman spectra to separate, identify the relatively weak Raman signal of a target analyte, and then model the changes to that signal to produce useful results for which actions can be taken. Raman spectroscopy is not a "plug and play" optical sensor technology due to (a) its ability to measure multiple constituents simultaneously as well as (b) the complexity of the samples/environment it is placed within. Raman probes placed directly into the sample (e.g., cell culture medium) provide a molecular fingerprint or "Raman signature" relating to the vibrational spectroscopic information for all the molecular components within the sample. Therefore, the raw spectroscopic data must be preprocessed to both enhance the analytes signal and reduce external noise from other species present in the raw data. The preprocessed data is then modeled using univariate and/or multivariate analysis approaches (often referred to as chemometric modeling), including but not limited to partial least squares (PLS), indirect hard modeling (IHM), principal component analysis (PCA), machine learning (ML) and any of its variants like deep learning (DL), artificial neural networks (ANN) and the like, to extract the maximum amount of relevant correlative information from the Raman spectral data. Using chemometric modeling, Raman analysis can provide multiple markers of the metabolic processes, which in turn, can be correlated and tracked in real-time both to offline measurements using known laboratory techniques mass spectrometry, gas chromatography-mass spectrometry (GC-MS), liquid chromatography-mass spectrometry (LC-MS), enzymatic methods and the like) and to non-specific online methods (e.g., a wide variety of absorption based techniques such as UV-Vis).

Raman spectroscopy has many unique advantages that make it ideally suited to process control applications. Numerous organic and inorganic materials may be non-destructively and non-intrusively investigated in solid, liquid and vapor phases, without sample preparation, often in real time. Excitation radiation and return, scattered radiation can be transmitted through wavelength-transmissive windows directly into and out of process vessels and via optical fibers over long distances for remote analysis. However, because the Raman effect is relatively weak, its applicability to certain in-line bioprocess control applications requiring fast acquisition times may be somewhat hindered, Reliable detection and quantification using Raman analysis requires sensitive and highly optimized instrumentation. Issues with fluorescence radiation generated within a sample by the excitation radiation and sample over-heating must also be considered.

Due to the weakness of the Raman effect, narrow-beam, high-intensity light sources (e.g., lasers) are one of the requirements needed to produce quality Raman spectra from a sample. To large extent, the resolution of the Raman spectrum relies on the bandwidth of the laser source used. Continuous wave laser sources are preferred, as pulsed lasers are more costly, more complex as well as utilize higher peak powers for sufficient signal-to-noise ratios, which can damage samples. The choice of light source wavelength depends on the requirements of a given application. Lower visible wavelengths and upper UV (e.g., approximately 300 nm to 500 nm) may induce strong autofluorescence in organic materials, which can mask the relatively weak Raman signal. As such, longer visible or near-IR sources (e.g., 633-1064 nm) may be better suited for organic targets. However, the Raman signal intensity is inversely proportional (to the fourth power) to excitation wavelength. Accordingly, longer wavelengths can require longer acquisition times, which can be problematic in certain bioprocessing applications.

There is a need for improvements in this area of technology for applying Raman analysis to fermentation processes.

SUMMARY

One aspect of the present disclosure discloses a method of characterizing and monitoring a fermentation process. In at least one embodiment of the present disclosure, the method comprises: acquiring online Raman spectra of a fermentation process within a fermenter vessel at different times during the fermentation process to generate a training data set; applying spectral preprocessing to the training data set such that non-correlative and covariant changes due to non-relevant species and/or properties are minimized and correlative changes due to a target analyte is amplified; acquiring physical samples from fermentation process near in time to the acquired Raman spectra; performing offline measurements of the target analyte properties and/or compositions using an assay measurement technique; generating a correlative model of the target analyte such that spectral changes in the training data set correlate with the offline measurements of the target analyte properties and/or compositions; acquiring online Raman spectra of a subsequent run of the fermentation process within the fermenter vessel at different times during the run to generate a process data set; and applying the correlative model to the process data set to qualitatively and/or quantitatively predict a value of a property and/or composition of the target analyte. The target analyte includes more than one species or property of the fermentation process.

In a further embodiment, the method further comprises acquiring offline Raman spectra from a predetermined set of the physical samples before or after online Raman spectra are acquired. In such an embodiment, data from the acquired offline Raman spectra are included in the training data set. In a further embodiment, the physical samples are acquired concurrently with the Raman spectra.

In embodiments of the present disclosure, the method further comprises preparing experimental samples and acquiring offline Raman spectra and offline assay measurements of the experimental samples, wherein data of the experimental samples are included in the training data set. In such an embodiment, the experimental samples are prepared according to a predetermined design of experiment in which selected analyte variables are prepared to predetermined values such that variance of the experimental samples is to statistically controlled.

In another embodiment, the spectral preprocessing includes a series of optimizations adapted to discern an optimal preprocessing algorithm for the fermentation process. In certain embodiments, the correlative model is generated using a univariate modeling methodology. In certain embodiments, the correlative model is generated using a multivariate modeling methodology.

In embodiments of the present disclosure, the method further comprises iteratively refining the correlative model using modeling statistics such that correlation of the training data set to the offline measurements is increased. In a further embodiment, the method comprises generating a signal, alarm or report when the value of the target analyte deviates from a desired range based on a threshold limit. In various embodiment, the target analyte includes at least one of ethanol concentration, fructose concentration, glucose concentration, degrees Brix value, NOPA value, pH value, ammonia concentration, tartaric acid concentration, malic acid concentration, total acidity value, citric acid concentration, acetic acid concentration, gluconic acid concentration, lactic acid concentration, glycerol concentration, sulfur dioxide concentration and polyphenolic content value.

In another aspect of the present disclosure, a computer program product comprises a non-transitory machine-readable storage medium encoding instructions that, when executed by one or more programmable processors, cause the one or more programmable processors to perform operations comprising: acquiring online Raman spectra of a fermentation process within a fermenter vessel at different times during the fermentation process to generate a training data set; applying spectral preprocessing to the training data set such that non-correlative and covariant changes due to non-relevant species and/or properties are minimized and correlative changes due to a target analyte is amplified; generating a correlative model of the target analyte such that spectral changes of the target analyte properties and/or compositions in the training data set corelate with offline assay measurements of physical samples taken from the fermentation process near in time to the acquired Raman spectra; acquiring a subsequent online Raman spectrum during a subsequent run of the fermentation process within the fermenter vessel; and applying the correlative model to the subsequent online Raman spectrum to qualitatively and/or quantitatively predict a value of a property and/or composition of the target analyte. In certain embodiments, the target analyte includes at least one of ethanol concentration, fructose concentration, glucose concentration, degrees Brix value, NOPA value, pH value, ammonia concentration, tartaric acid concentration, malic acid concentration, total acidity value, citric acid concentration, acetic acid concentration, gluconic acid concentration, lactic acid concentration, glycerol concentration, sulfur dioxide concentration and polyphenolic content value. In at least one embodiment, the operations further comprise generating a signal, alarm or report when the value of the target analyte deviates from a desired range based on a threshold limit.

In another aspect of the present disclosure, a Raman analysis system comprises: a light source configured to emit excitation light; an optical probe coupled to the light source via an optical cable such that the excitation light is emitted from a probehead of the probe into a sample volume, wherein the probe is configured to receive and transmit a Raman signal from the sample volume via the optical cable or another optical cable; a spectrograph configured to spectrally separate the transmitted Raman signal; a detector configured to receive the separated Raman signal and convert the separated Raman signal into a Raman spectrum; and a controller configured to: acquire online Raman spectra of a fermentation process within a fermenter vessel at different times during the fermentation process by actuating the light source to emit the excitation light and receiving the Raman spectrum from the detector; apply a correlative model to the Raman spectrum to qualitatively and/or quantitatively predict a value of a property and/or composition of a target analyte, wherein the correlative model is adapted such that spectral changes of the target analyte properties and/or compositions in previously acquired Raman spectra correlate with offline assay measurements of physical samples taken from a previous fermentation process; and monitor the fermentation process by periodically acquiring subsequent online Raman spectra.

In an embodiment, the controller is further configured to generate a signal, alarm or report when the value of the target analyte deviates from a desired range based on a threshold limit. In certain embodiments, the target analyte includes at least one of ethanol concentration, fructose concentration, glucose concentration, degrees Brix value, NOPA value, pH value, ammonia concentration, tartaric acid concentration, malic acid concentration, total acidity value, citric acid concentration, acetic acid concentration, gluconic acid concentration, lactic acid concentration, glycerol concentration, sulfur dioxide concentration and polyphenolic content value

DESCRIPTION OF THE DRAWINGS

The described embodiments and other features, advantages and disclosures contained herein, and the manner of attaining them, will become apparent and the present disclosure will be better understood by reference to the following description of various embodiments of the present disclosure taken in junction with the accompanying drawings, wherein.

DETAILED DESCRIPTION

Figure 1:
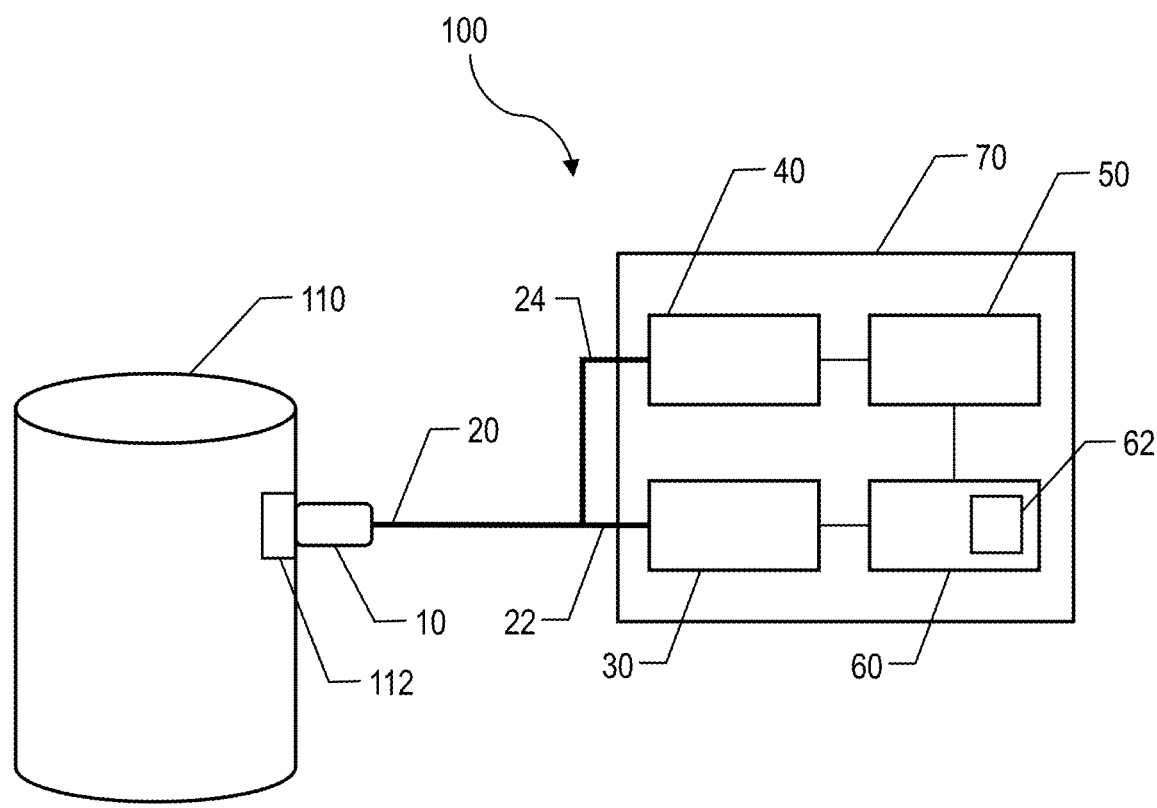
FIG. 1 is a schematic representation of an embodiment of a Raman analysis system according to the present disclosure.

The present disclosure includes the use of dispersive Raman spectroscopic analysis to perform real-time, non-destructive compositional analysis for wine production, grape juice fermentation in particular. Conventionally, aside from macro-scale process parameters such as pH, temperature, dissolved oxygen and dissolved carbon dioxide, the analytes involved in the wine fermentation process are infrequently measured because testing must be done offline. For example, pH, which is frequently measured online, is typically calibrated for drift via an offline assay. Due to collection time, personnel and cost, offline analytics continuous acquisition is impractical. These limitations deprive a winemaker of the ability to observe, measure and correct real-time process deviations, which could lead to product quality issues and decreased yields. Creating a wine's uniqueness and ensuring the final product matches the desired taste profile requires monitoring inputs to the process and each stage of process. Variations in grape juice attributes and other inputs such as bacteria and yeast (e.g., natural and/or artificial) can significantly impact a wine's quality. Of the stages of winemaking, fermentation is the most variant, making monitoring and control critical.

The present disclosure includes methods for using Raman analysis to model and determine the presence and concentration of multiple analytes within the grape juice fermentation process while the fermentation process is in progress (i.e., online). Using the disclosed methods, the analyte determinations may be performed in real time in a non-destructive and immersive way within the fermenter without any sample preparation for Raman analysis. The disclosed methods have proven effective in modeling and real-time prediction of multiple compositional characteristics during several fermentation validation varietal-specific batches (e.g., chardonnay and pinot noir varietals), and/or as combined into a generic model, which can be applied in a non-varietal-specific manner. The present disclosure enables a wine producer to monitor and adjust process-specific parameters of the fermentation process to fine-tune product quality and yields in real-time both throughout the wine production process and in the end product. The present disclosure further enables reduced production costs in manufacturing, real-time fault monitoring for non-ideal batches, and improved critical quality attributes of the product manufactured.

During the grape juice fermentation step of wine production, there are several key analytes that indicate the quality of the current batch. Some of these key analytes include ethanol concentration, fructose concentration, glucose concentration, degrees Brix (i.e., total dissolved sugar content by mass), the level of available nitrogen given by o-phthaldialdehyde assay (NOPA), ammonia, pH, tartaric acid, malic acid, total acidity, citric acid, acetic acid, gluconic acid, lactic acid, glycerol, sulfur dioxide, polyphenolic content and total phenolic concentration. These exemplary species, among others, are recognized as being important in the manufacturing of wine (e.g., reds, whites, rose and orange). Having real-time, online measurements for feedback control and quality control purposes, improves yields and expedites the detection of quality issues during the fermentation process.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

According to at least one embodiment of the present disclosure, as shown in FIG. 1, a Raman system 100 for monitoring a fermentation process may include a fiber-coupled Raman probe 10, which is configured and arranged to transmit excitation light into the fermentation process under test within a fermentation vessel 110 under test and to collect a Raman signal emitted from a sample volume within the fermentation vessel. The probe 10 may be coupled to an excitation light source 30 by a fiber optic cable 20 such that excitation light emitted by the light source 30 is incident upon a sample within the sample volume via a process connection 112. In at least one embodiment, the process connection 112 includes an opening and is configured to enable attaching the probe 10 to the fermentation vessel 110 such that the probe 10 is in direct contact with the sample via the opening of the process connection 112. In a further embodiment, the process connection 112 may include a window that is transparent to the excitation light of the light source 30 such that the probe 10 is in indirect contact with the sample via the window of the process connection 112. In certain embodiments, the process connection 112 is any suitable means of arranging the probe 10 such that the excitation light is incident upon the sample and the resulting Raman signal is incident upon the probe 10. The probe 10 and fiber optic cable 20 enable the Raman system 100 to excite the sample volume and collect the resulting Raman signal in situ within the fermentation vessel 110 while the fermentation process is in progress, thereby generating real-time data from the fermentation process in progress in a production-scale environment.

The probe 10 may be any suitable, commercially available Raman probe, including those manufactured and sold by Kaiser Optical Systems, Inc. of Ann Arbor, Mich. (Applicant). The probe 10 may include a probehead in which various optical components are housed including, as non-limiting examples, sampling optics, gratings, filters, beam combiners and connectors configured to join the various optical components with the fiber optic cable 20. The fiber optic cable 20 may include a multi-mode fiber or a single-mode fiber, either of which is configured to provide an excitation path from the light source 30 to the probe 10, which transmits the excitation light to the sample, and a collection path from the probe 10 to a Raman instrument 70, which transmits scattered light containing the Raman signal from the sample to the Raman instrument 70. In at least one embodiment, the fiber optic cable 20 may include an excitation cable 22 for the excitation path and a separate collection cable 24 for the collection path in which the excitation and collection paths may be combined at or in the probe 10 using a combination of optical components including, for example, a grating and a beam combiner. For example, a beam combiner (e.g., a holographic beam combiner) in the probe 10 may be used to combine the excitation path onto a common optical axis with the collection path such that a common sampling optic in the probe 10 may be used for both paths.

In at least one embodiment, the Raman system 100 configured for process monitoring applications may include significant lengths (e.g., hundreds of meters) of the fiber optic cable 20 between the Raman analyzer 70 and probe 10. Each optical fiber has its own Raman and elastic scattering signatures, which may be removed at the probe 10 before the excitation is emitted into the sample, for example, via the excitation cable 22. For example, the strong light source line due to Rayleigh scatter (i.e., the Rayleigh line) from the sample may be removed from the collected Raman signal at the probe 10 before entering the fiber optic cable 20 (e.g., the collection cable 24). Otherwise, the Rayleigh line may generate a competing fiber signature en route to the spectrograph 40. In certain embodiments, a holographic grating and/or spatial filter may be inserted into the excitation path to remove the fiber signature. The Rayleigh line may be removed from the collected Raman signal by a notch filter (e.g., a holographic notch filter) in the collection path.

In certain embodiments, the Raman system 100 may be configured to monitor multiple sample locations in a process. In such an embodiment, multiple remote probes 10 may be coupled to a single Raman instrument 70 via multiple fiber optic cables 20. As shown in FIG. 1, the Raman instrument 70 may include the light source 30 and a spectrograph 40 configured to spectrally separate the Raman signal transmitted via the fiber optic cable 20 and to feed the spectrally separated Raman signal to a detector 50 of the Raman instrument 70 via optical components of the spectrograph 40. The Raman system 100 is a dispersive Raman system and includes a diffraction grating and corresponding optical components to disperse (e.g., spectrally separate) the Raman signal onto the detector 50. As a dispersive system, the Raman system 100 does not require moving components that can be affected by environmental conditions and other known disadvantages as such alternative systems as Fourier Transform Raman spectroscopy, for example.

The light source 30 may be a narrow-band, high-intensity light source including, but not limited to a laser, a laser diode, neon-tungsten lamp, mercury lamp or the like. The detector 50 may be an array detector (e.g., multi-channel) such as, but not limited to, a charge-coupled device (CCD) or a semiconductor array (e.g., a germanium or indium gallium arsenide (InGaAs) detector). In certain embodiments, the Raman instrument 70 may include a notch filter, an edge pass filter, a band pass filter and/or other optical components configured and arranged to remove the strong, elastically scattered (unshifted) Rayleigh component of the light transmitted to the spectrograph 40 that would otherwise hide (e.g., as noise) the relatively weak Raman signal. In embodiments employing multiple probes 10, the Raman instrument 70 may include a sequencer or splitter to multiplex the output of the light source 30.

The Raman instrument 70 may further include a controller 60 running software 62 configured to control the Raman system 100, including the light source 30, spectrograph 40 and detector 50, and to receive and analyze detector data from the detector 50 in communication therewith. The controller 60 may be configured for data acquisition and signal processing of the detector data to execute the methods of the present disclosure. The controller 60 may be configured to perform certain operations comprising a control structure to provide the functions described herein. In certain embodiments, the controller 60 forms a portion of a processing subsystem that includes one or more computing devices having memory, processing, and/or communication hardware. The controller 60 may be a single device housed within the Raman analyzer 70 or a distributed device, and the functions of the controller 60 may be performed by hardware and/or software. The controller 60 can include one or more Arithmetic Logic Units (ALUs), Central Processing Units (CPUs), memories, limiters, conditioners, filters, format converters, or the like which are not shown to preserve clarity. In at least one embodiment, the controller 60 is programmable to execute algorithms and processes data in accordance with operating logic that is defined by programming instructions, such as software or firmware. Alternatively or additionally, operating logic for the controller 60 can be at least partially defined by hardwired logic or other hardware, for example, using an Application-Specific Integrated Circuit (ASIC) of any suitable type. The controller 60 can be exclusively dedicated to the functions described herein or may be further used in the regulation, control, and activation of one or more other subsystems or aspects of the Raman system 100.

The controller 60 may include one or more modules structured to functionally execute the operations of the controller 60. The description herein including modules emphasizes the structural independence of the aspects of the controller 60 and illustrates one grouping of operations and responsibilities of the controller 60. Other groupings that execute similar overall operations are understood to be within the scope of the present disclosure. Modules may be implemented in hardware and/or software on computer readable medium, and modules may be distributed across various hardware or software components.

The Raman system 100 is capable of both remotely delivering the excitation light to a particular process location and remotely collecting the Raman signal. With the ability of the Raman system 100 to detect chemical and physical information characteristic of a substance, when the probe 10 is used to analyze the fermentation process, the chemical and physical information can be gathered in real-time, at any point in the process and in a non-destructive manner.

In embodiments of the present disclosure, this real-time information feedback provides several advantages, including: (1) real-time feedback control of the fermentation process by monitoring actual chemical, physical and compositional information; (2) real-time predictive determination of both the starting and end-point for individual properties; (3) end-of-batch property determination to forgo additional offline testing, thereby enabling real-time product release; and (4) the ability to compose and apply both specific and universal, non-varietal specific, scale transferable models for prediction of each analyte within a future fermentation process.

With the capability to collect spectral signatures of multiple physical and chemical properties in real time within the same spectrum, embodiments of the Raman system 100 extract quantitative compositional, chemical and physical information regarding various process parameters and several key analytes. If subsequent offline assay reference measurements are made, correlations may be established with respect to a composition and/or a particular property and how those relative changes relate to the acquired Raman spectrum, whether the spectrum was acquired in real time or post run.

Such correlations may be conducted in a univariate and/or multivariate space to relate online Raman spectral acquisitions to a discreet quantifiable compositional, chemical and physical properties acquired offline via fermentation assay measurements. Spectral preprocessing, along with multivariate analysis, such as PLS, PCA, ML, DL, ANN and/or IHM, for example, provides information that may be plotted on a time scale to inform and alert an operator, in real time, of the quantifiable and/or the relative status of important constituents during and after the fermentation process.

According to an embodiment of the present disclosure, during one or more fermentation batches (e.g., individual instances of the fermentation process from start to finish), Raman spectra are acquired at specified intervals during each run from the fermentation vessel 110 using the Raman system 100. During and/or after the fermentation process, a number of samples are quantitatively measured via offline assays. At the specific sampling times, the acquired Raman spectra of the samples are used to build one or more quantitative models that correlate each composition and/or property to the Raman spectral changes (e.g., peaks and valleys) occurring within a particular run or batch. In a possibly less correlative modality (relative to online measurements), samples may be analyzed by Raman analysis offline and then correlated to their respective offline assay values. After the quantitative model is generated, the model may be applied in real time using an embodiment of the Raman system 100, including the probe 10 in communication with the fermentation process being characterized, monitored and controlled.

Figure 2:
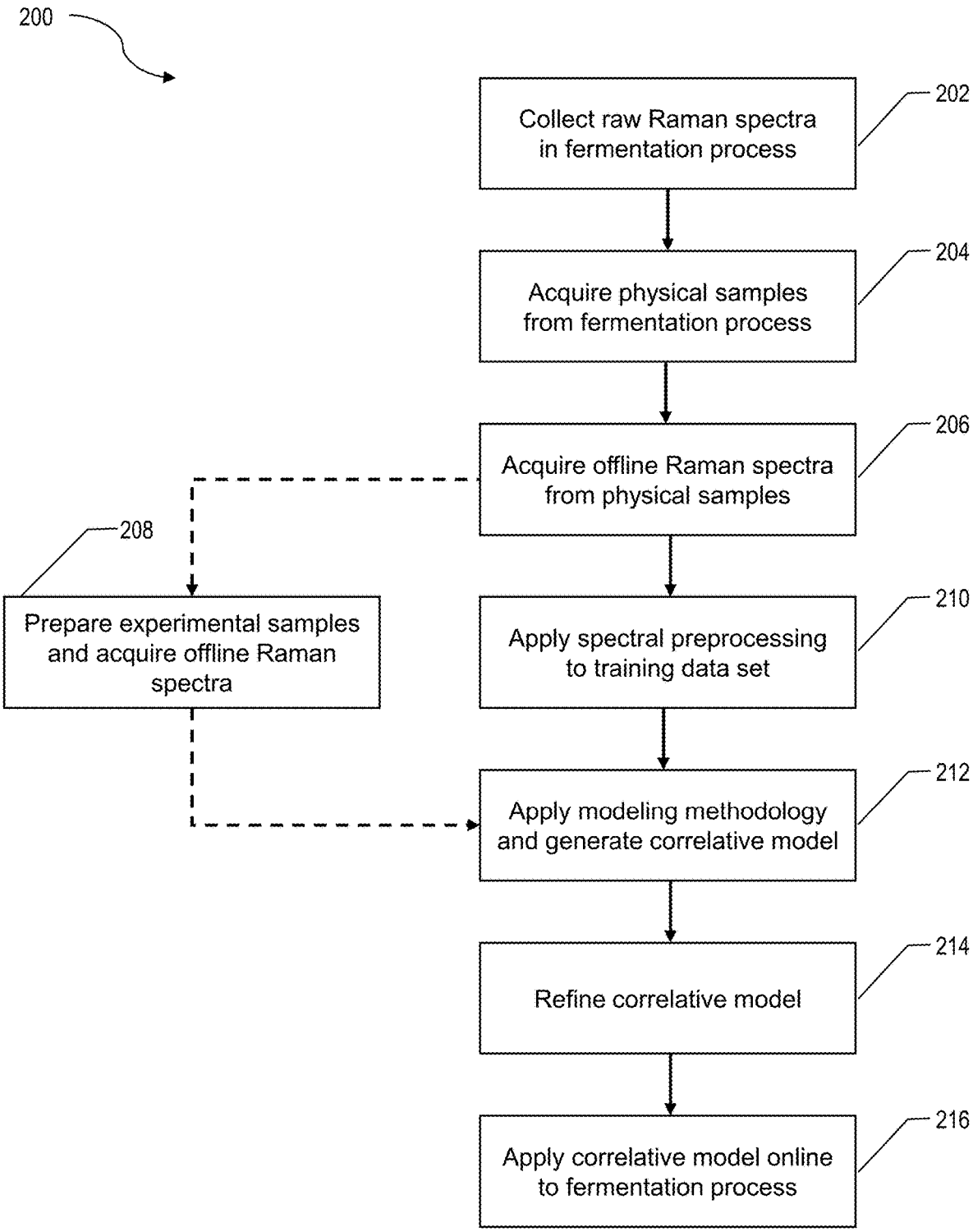
FIG. 2 shows an embodiment of a method according to the present disclosure.

According to at least one embodiment of the present disclosure as shown in FIG. 2, a method 200 of characterization, monitoring and controlling a fermentation process under test includes generating a training data set, developing a chemometric, correlative model using the training data set, validating the model and applying the model to future production fermentation process batch runs to characterize, monitor and control the production fermentation batch. The method 200 may include a step 202 of generating the training data set by spectrally collecting a statistically large set of online process spectral measurements of raw Raman spectra at different points in time while the fermentation process is in progress from a fermenter (e.g., the fermentation vessel 110 of FIG. 1) using the Raman system 100. The process measurements comprising the training data set include spectral variances of the constituents of the process within the fermenter during the fermentation process, including the analyte properties and compositions to be predict in future batches. Variance in the analytes enables the development of a robust model capable of accurately and precisely predicting future analyte properties and compositions within a range that will be measured in future batch runs. The online process measurements may be time stamped by facilitate correlation to offline measurements. The online process measurements may be captured using a pre-determined amount of total acquisition time selected to generate a signal-to-noise ratio which is sufficient to produce the required measurement accuracy and precision.

Natural variance between fermentation batches lead to absolute differences in both Raman and autofluorescence signals acquired during a Raman exposure. For example, variance between grape varietals and growing conditions create variation in the concentrations of different sugars in the grape juice inputs to the fermentation process. The step 202 may require the Raman spectral exposure be dynamically adjusted for an optimized value during online sampling of the fermentation batch due to such natural variance. In addition, the precision of the Raman model is dependent on the quality of the Raman spectral data within the training date set. To produce data that is precise for a given set of requirements, the Raman signal may be maximized (to a point) whereas the noise of that measurement is reduced (to a point) as to provide an adequate signal-to-noise ratio (S/N ratio). A Raman absolute signal is linearly related to total acquisition time, which is defined as the total amount of acquisition time in building one individual Raman spectrum from one or more exposures. A conventional rule of thumb instructs an operator to select an exposure time the is long enough to provide an adequate S/N ratio given the rate of change of the species (e.g., analytes) measured (sometimes called "temporal error"). To reduce the temporal error in predicted values from the Raman model, the selected total acquisition time should be optimized around the various rates of change of the measured analytes within the fermenter, knowing Raman analysis has an averaging effect of the predicted value over the time of the measurement. After the exposure and total acquisition time settings are determined given the desired precision and optimized in view of the rate of change of the measured analytes, online process spectral measurements that capture the variance taken and analyzed to develop the model.

Depending upon the requirements of the Raman method, in at least one embodiment, a statistically large set of process samples may include a variety of independent samples of the fermentation process to enable one to predict a process value in which the variation in the modeled amounts and effects are less than 10% relative error to the "true" accepted value at that point in time. In other embodiments, the a statistically large set of process samples may include enough independent samples of the process to enable one to conclude the variation in the modeled amounts and effects are at or under 5% relative error.

The method 200 may include a step 204 of acquiring physical samples during the fermentation process (e.g., from the fermentation vessel 100) and performing offline measurements of the analyte properties and/or compositions using an offline assay measurement device conventionally used to produce these values, including those prior art (e.g., non-Raman) devices and means described herein. As a non-limiting example, physical samples may be acquired from the fermentation process batch every two hours over the course of 2-4 days as the process progresses. In at least one embodiment, the physical samples may be conditioned to arrest the fermentation process as to maintain the properties and compositions present at the time the sample was taken from the fermenter 100. For example, a sample may be taken from the fermenter 100 and placed in a centrifuge or otherwise filtered to separate the active yeast from the other constituents, thereby stopping the fermentation process with the sample. As a further example, the sample may be refrigerated and frozen was stop the fermentation process until the offline assay measurements are performed. In at least one embodiment, the physical samples are taking from the fermentation process at or near in time when the online process spectral measurements of step 202 are collected. In at least one embodiment, the online process spectral measurements of step 202 may be collected concurrently with the physical samples of step 204. Data from the step 204 is added to the training data set.

According to at least one embodiment of the present disclosure, method 200 may include a step 206 of acquiring offline Raman spectra from a predetermined set of the physical samples before or after online spectra is acquired. In an embodiment, the step 206 may be performed when the physical samples collected online lack the variance needed for robust predictive process variable models. The physical samples selected should have a variance in at least one or more of the key process variables (e.g., analyte property and/or composition) for which Raman analysis will be used for real-time monitoring during production fermentation. The offline spectra can be from sample retains from various time points in previous fermentations. Sample retains include physical samples taken from past fermentation batches and conditioned for storage. Such samples retains provide a record of past batches. Data from the step 206 may be added to the training data set.

Alternatively, additionally or optionally, in an embodiment, the method 200 may include a step 208 of preparing (e.g., formulating) experimental samples and acquiring offline Raman spectra and offline assay measurements of the experimental samples. For example, the experimental samples may be created by adjusting the properties or compositions of the species within selected sample retain, conventionally referred to as "spiking." Such adjusting may include increasing or decreasing the presence or concentration of an analyte of interest. In at least one embodiment, adjusting the sample retains may follow a predetermined design of experiment (DoE) in which selected process variables (e.g., analyte concentration) are purposefully and specifically set to predetermined values to statistically control the variance of the experimental samples and thereby determine the relative of effects of the variances, including correlated effects. Spiking may be used to expand the range of statistical models, to help mitigate Raman signal covariance between species in the fermenter, and to assist in modeling by amplifying Raman signal variances for correlation to individual offline assay values using a pre-determined amount of total acquisition time selected to generate a signal-to-noise ratio which is sufficient to produce the required measurement accuracy and precision. Data from the step 208 may be added to the training data set.

The method 200 further includes a step 210 of applying spectral preprocessing to the Raman spectral training data set to minimize non-correlative and covariant spectral variances of non-relevant species and properties (e.g., from species/analytes that are not of interest) across the Raman spectrum, while at the same time amplifying correlative changes due to the process variable(s) of importance (e.g., target analytes). Spectral preprocessing may include mathematical manipulations of the training data set to increase spectral variance of a particular property or set of properties of the analyte of interest. In an embodiment, a series of optimizations are performed to discern the optimal preprocessing algorithm for a particular fermentation process. The spectral preprocessing may include a series of processes that can vary from data set to data set but may follow a series of rules and standard mathematical tools known to one of skill in the art.

A step 212 of the method 200 includes determining whether to use a univariate or multivariate modeling methodology and applying the selected methodology to generate a correlative model that relates spectral changes (e.g., peaks and valleys) in the preprocessed Raman spectral data acquisitions (e.g., spectral variances) from step 202 to changes observed in the values from the offline assay measurements from step 204 using conventional techniques. For example, the complexity of the fermentation process analyte constituent system, the quality of the Raman analyte peaks within the data, and/or the degree of spectral peak overlap may determine which modeling methodology is selected. Due to the inherent complexity of fermentation spectra, multivariate statistical modeling techniques may be more often applied relative to univariant techniques. The step 212 includes calculating a linear and/or non-linear correlation of the preprocessed Raman spectral data of the training data set to the values from the offline assay measurements for the analytes of interest to modeled. In an embodiment, the selected methodology may be applied to the offline Raman spectral data acquisitions of step 206 in addition to the spectral data of step 202. The correlative model may include one or more analytes of interest depending on the scope of the Raman spectral data and the offline assay measurements. In an exemplary embodiment, a separate correlative model is generated for each analyte of interest. In such an embodiment, each separate model may be applied to the same preprocessed Raman spectral data. In a further embodiment, raw spectral Raman data may be acquired using different conditions that depend on a given target analyte and selected to optimize the quality of the spectral data relative to the target analyte.

When a statistically representative amount of Raman spectral data is captured and time matched to the offline assay measurement values, robust correlations are formed for which future predictions can be made when using the methods of the present disclosure to monitor the process. The robustness of correlative model is affected by the training data set and, for example, to the degree to which the training data set includes sufficiently variant spectra-assay combinations to capture the range of chemical, physical and compositional changes within the fermenter from beginning to end of the fermentation process. This variance can be captured via natural and/or artificial means (e.g., using the step 208), as long as the samples represent the conditions within the fermenter, as described herein.

A step 214 of the method 200 includes iteratively refining the correlative model using modeling statistics to enhance correlation of the Raman spectra to the offline assay measurements values and/or reduce noise, bias and/or other unwanted artifacts in the correlative model. For example, the correlative model may be refined using statistical plots that show both the relative spectral residual and the concentration residual remaining from the Raman prediction. In addition, plots that display in (modeling) space vs. out of (modeling) space error of the predicted value may be utilized.

The step 214 may further include validating the correlative model by repeating at least steps 202 and 204 on one or more fermentation processes and assessing the whether the correlative model is adequately predictive. In such an embodiment, validation Raman spectra are acquired from the fermentation process and compared to the corresponding validating offline assay measurements. A separate training data set (e.g., a "validation" training data set) need not be prepared. In a further embodiment, the validation Raman spectra from the step 214 and the corresponding offline assay measurements may be added to the training data set and the remaining steps of the method 200 to further refine and improve the robustness of the correlative model. For example, when the validation Raman spectra include variances in the analytes of interest outside those present in the training data set, the training data set may be updated and the correlative model refined to include and model those variances, thereby improve the robustness of the correlative model.

The method 200 may further include a step 216 of applying the correlative model to subsequent online and/or offline data sets from future fermentation batches as to qualitatively and/or quantitatively predict analyte values (e.g., properties and or compositions) of interest from real-time, Raman spectral data collected from the future fermentation process in progress, for example, using the Raman system 100. In the context of the present disclosure, a "prediction" is a conversion of Raman spectral data from online Raman analysis measurements using the correlative model to estimate or predict the true value of the property (or properties) of the analyte(s) of interest (e.g., chemical, physical and/or compositional). In an embodiment, predicted analyte values may be used to monitor the fermentation process in real time, without the need for offline measurements (e.g., by either Raman analysis or assay measurements) to alert an operator or a process control system that the analyte value has deviated from a desired range (e.g., over time based on a threshold limit). In such an embodiment, the step 216 may include generating a signal, alarm or report to the operator of process control system using the Raman system 100. The step 216 may further include performing an action to correct or compensate for the analyte value deviation or to abort the fermentation process based on the alert generated. One skilled in the art can identify other actions that may be performed based on the predicted analyte values, and such actions are within the scope of the present disclosure.

The method 200 of the present disclosure can provide real-time information about the fermentation process, enabling immediate adjustments to be made, for example, via a feedback loop step, to correct the properties and/or values of the constituents if any deviate from a desired or planned trajectory, which can lower costs and/or improve the quality of production. Additionally, the properties and/or values of the constituents will be known (at least as an aggregate) at the end of a particular batch such that additional offline measurements (e.g., quality control checks) need not be performed, further lowering costs.

During a fermentation process, using the methods of the present disclosure, the acquiring of Raman spectra should be set to a total acquisition time as to provide a certain level of precision with respect to a predicted or set of predicted chemical or physical measurement(s) following preprocessing and modeling, whether an univariate or a multivariate methodology is used. Each Raman spectra contains several spectral signatures from these chemical, physical and compositional properties to various signal-to-noise ratios, depending on the strength of the signal associated with a given property and on the noise within the spectrum at the relevant wavelength positions in the spectrum. Once spectral preprocessing is applied, as in steps 210, the signals are then related to changes that occur in each property within the data set.

Chemometric modeling can often be influenced by the scale of the process being monitored. However, scale-independent multivariate models based on Raman spectral data obtained from bioreactor cultures of one or more different scales can be developed such that models based on Raman spectral data obtained at test scales (e.g., bench and/or pilot-scales) are accurate and precise at larger manufacturing-scale (e.g., 1000 L or greater) settings (see, e.g., U.S. Ser. No. 10/563,163), Likewise, accurate and precise, scale-independent, multivariate models based on Raman spectral data from fermentation processes of one or more different scales can be developed. Model development using smaller scale test reactors is generally faster and less costly, allowing more parameters to be tested and modeled often for a lower cost. By developing multivariate models based on Raman spectral data obtained across multiple different scales of fermentation processes, accurate determination of key process parameters across a range of scales, including manufacturing-scales, is practical.

The systems and methods of the present disclosure has been applied to grape juice fermentation in a manufacturing-scale, production wine production process. Consequently, Applicant has determined that after pretreatments, several key analytes, including ethanol, fructose, glucose, degrees Brix, NOPA, pH, ammonia, tartaric acid, malic acid, total acidity, citric acid, acetic acid, gluconic acid, lactic acid, glycerol, pH, sulfur dioxide and polyphenolic content can be determined in real time during the in situ measurement of the fermentation process using embodiments of the Raman system 100 and the method 200 disclosed herein. Nonetheless, one skilled in the art having the benefit of the present disclosure will recognize that other analytes are possible. The resulting correlative models demonstrated sufficient correlation over multiple fermentation batches for multiple wine grape varietals—chardonnay, merlot, riesling and pinot noir—using a general, base model applicable to one and/or all grape varietals. Correlation of the correlative model was demonstrated using such known statistical metrics as a coefficient of determination ($R^2$) and chemometric scores and loadings. In certain embodiments, other statistical metrics may be used including, but not limited to, root mean square error of validation (RMSEV), root mean square error of cross-validation (RMSECV), root mean square error of prediction (RMSEP), standard error of prediction (SEP), residual predictive deviation (RPD) and standard deviation (SD).

Figure 3:
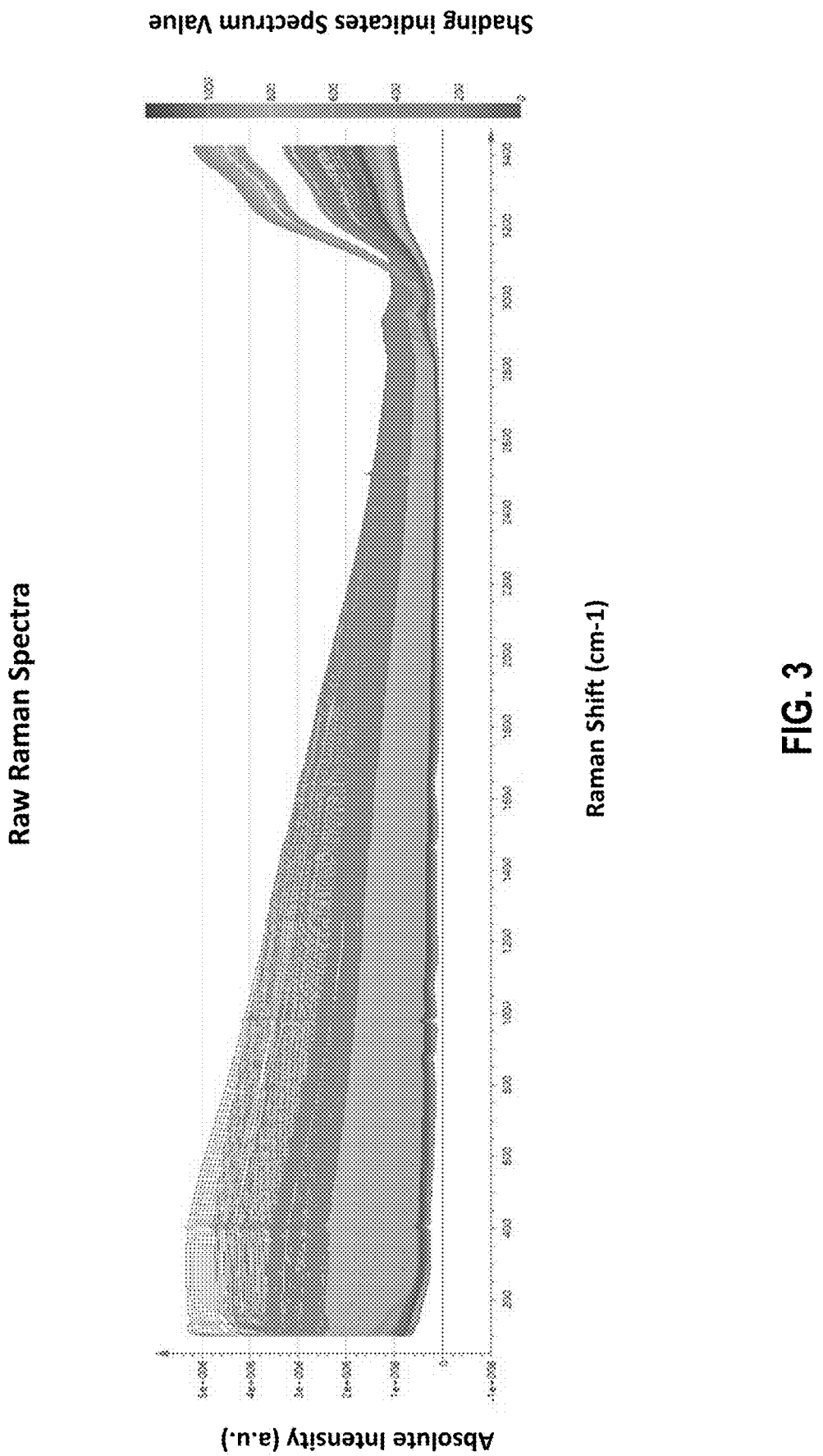
FIG. 3 shows a plot of raw Raman spectral data of multiple fermentation batches according to the present disclosure with absolute intensity in arbitrary units (a.u.) versus Raman shift ($cm^{-1}$)
Figure 4:
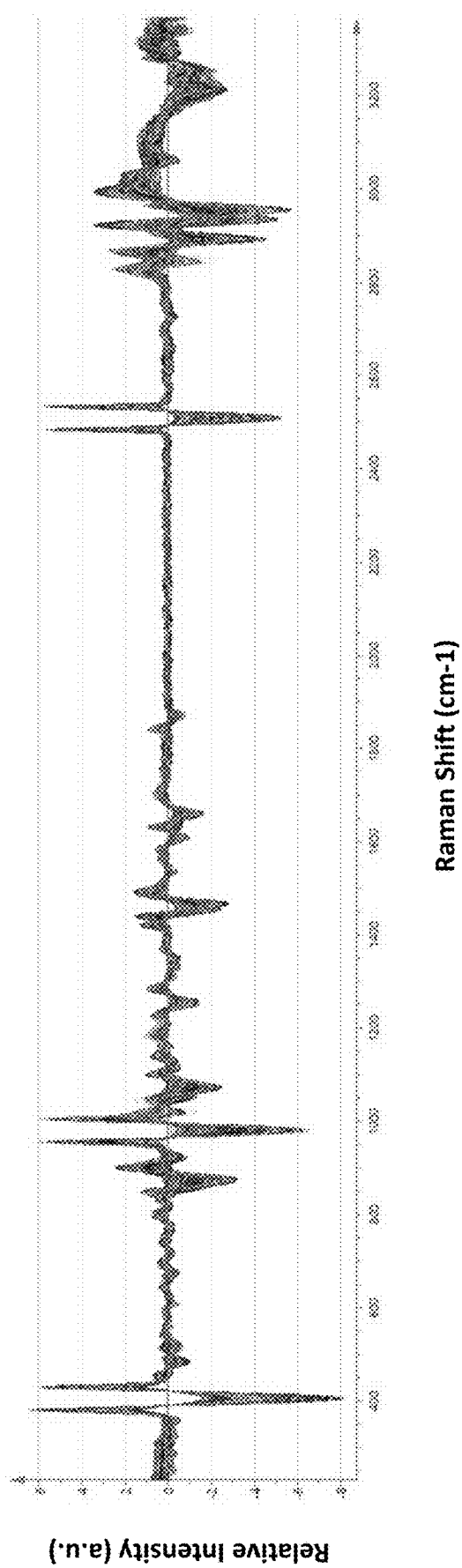
FIG. 4 shows a plot of preprocessed Raman spectral data for multiple fermentation batches according to the present disclosure with relative intensity in arbitrary units (a.u.) versus Raman shift ($cm^{-1}$)
Figure 5:
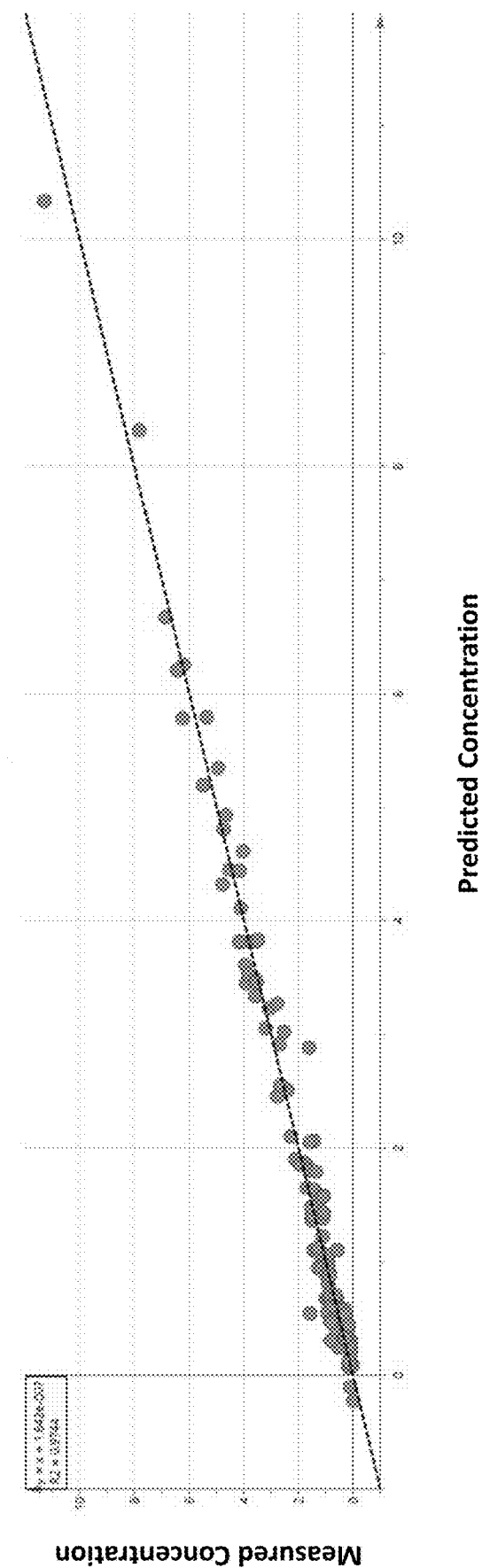
FIG. 5 shows a plot of a linear regression of an ethanol concentration prediction using an ethanol correlative model according to the present disclosure with measured ethanol concentration (% v/v) versus predicted ethanol concentration (% v/v)

FIGS. 3 and 4 show examples of raw and preprocessed Raman spectra acquired throughout several batches of a fermentation process of grape juice using the Raman system 100. FIG. 3 presents raw Raman spectral data in which the gray-scale shading of each curve a given batch over time. FIG. 4 presents preprocessed Raman spectra, again, data in which the gray-scale shading of each curve presents a given batch over time. The raw spectral data, acquired every 10 min., contains the raw spectral variance of both the captured analyte information within the batch (at each specific time point) and unwanted variation from other sources present in the process. To isolate and correlate the molecular signatures of interest, which include the desired compositional information of analytes of interest, spectral preprocessing was performed to remove unwanted variance and to amplify the spectral signatures of the analytes contained within the Raman spectrum as the batch evolved. The spectral changes (i.e., peaks and valleys) of the preprocessed spectra indicate changes analyte concentrations.

As an example, multivariate PLS analysis was performed on the preprocessed spectra of FIG. 4, which contain the multiple component spectral signatures, to extract each specific analyte of interest. In this example, the PLS algorithm was configured to statistically compare the changes from the known concentration values of ethanol (e.g., acquired from the offline assays as described herein) with the online Raman spectral changes and, further, to determine how strong the correlation exists between both variances. The PLS algorithm was configured to deconstruct the changes into correlation metrics, which were plotted to identify relationships and to determination and/or assess the quality of the base model. FIG. 8 shows a linear regression of ethanol concentration between the offline assay values and predicted values using the validated correlative model. As shown in FIG. 8, the prediction precision or error across the range of ethanol concentrations is essentially zero, having a coefficient of determination ($R^2$) of 0.974 or approximately 1.0. In the context of the present disclosure, a "prediction" is a conversion of Raman spectral data from online Raman analysis measurements using the correlative model to estimate or predict the true value of the property of the analyte of interest.

Figure 6:
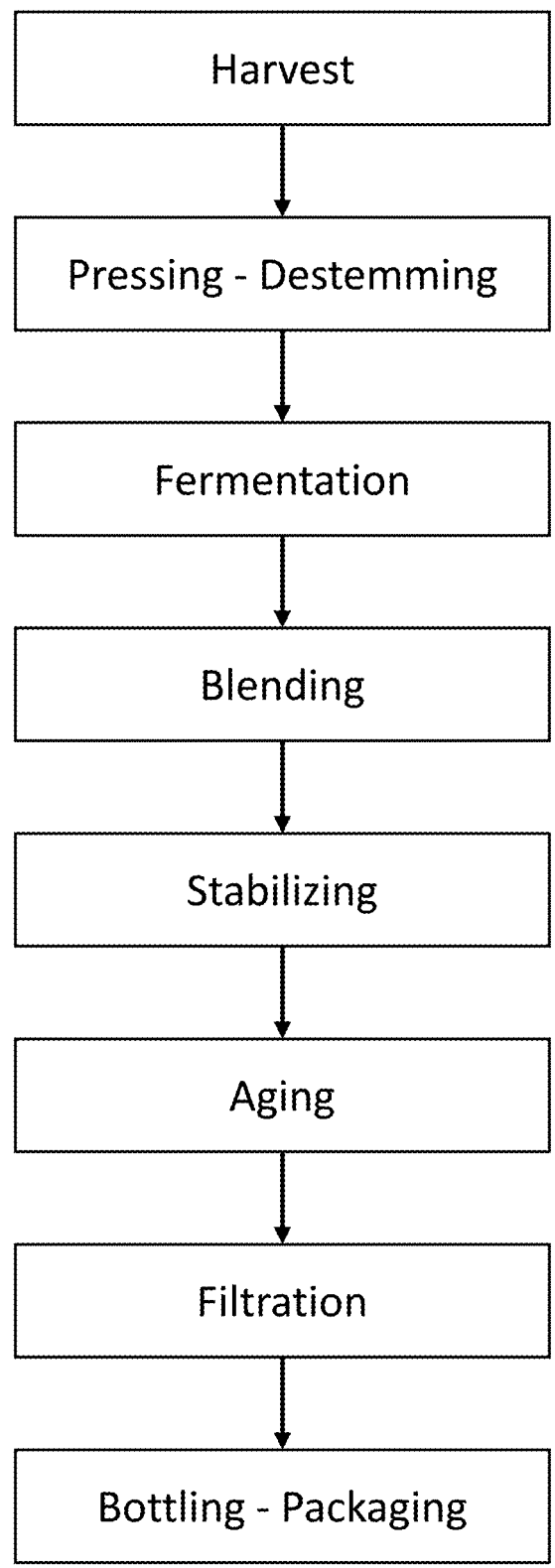
FIG. 6 shows a schematic illustration of a wine making process.

Though the fermentation process is one contributor to the character and quality of a finished wine, the Raman system 100 and the method 200 may be applied to any stage of the wine making process, as shown schematically in FIG. 6. For example, the Raman system 100 can be applied to assess properties of the grapes themselves—either on the vine before harvest or after harvest. Moreover, the Raman system 100 can be applied to characterize properties of multiple batches of input fermented grape juice to facilitate the blending of wines. Further, the Raman system 100 can be applied to the stages of stabilizing, aging and filtration of the wine to monitor its properties and quality prior to and after bottling and final packaging. At each stage, a correlative model may be developed using an embodiment of the method 200 to model the process at the target stage by acquire Raman spectra at that stage and correlating the acquired Rama spectra to offline assay measurements and/or to known standard samples, as described herein in the context of the fermentation process. Consequently, at each stage, corrective actions may be taken based on the real-time, predictive values from online monitoring of each stage to improve quality, avoid lost batches and lower overall cost for the entire wine making process.

While various embodiments of a Raman spectroscopic analysis system and methods generating chemometric models for using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. The present disclosure is not intended to be exhaustive or to limit the scope of the subject matter of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible and thus remain within the scope of the present disclosure.

The invention claimed is:

1. A method of characterizing and monitoring a fermentation process, the method comprising:
acquiring online Raman spectra of a fermentation process within a fermenter vessel at different times during the fermentation process to generate a training data set;
applying spectral preprocessing to the training data set such that non-correlative and covariant changes due to non-relevant species and/or properties are minimized and correlative changes due to a target analyte is amplified;
acquiring physical samples from fermentation process near in time to the acquired Raman spectra;
performing offline measurements of the target analyte properties and/or compositions using an assay measurement technique;
generating a correlative model of the target analyte such that spectral changes in the training data set correlate with the offline measurements of the target analyte properties and/or compositions;
acquiring online Raman spectra of a subsequent run of the fermentation process within the fermenter vessel at different times during the run to generate a process data set; and
applying the correlative model to the process data set to qualitatively and/or quantitatively predict a value of a property and/or composition of the target analyte.

2. The method of claim 1, wherein the target analyte includes more than one species or property of the fermentation process.

3. The method of claim 1, the method further comprising acquiring offline Raman spectra from a predetermined set of the physical samples before or after online Raman spectra are acquired.

4. The method of claim 3, wherein data from the acquired offline Raman spectra are included in the training data set.

5. The method of claim 1, wherein the physical samples are acquired concurrently with the Raman spectra.

6. The method of claim 1, the method further comprising preparing experimental samples and acquiring offline Raman spectra and offline assay measurements of the experimental samples, wherein data of the experimental samples are included in the training data set.

7. The method of claim 6, wherein the experimental samples are prepared according to a predetermined design of experiment in which selected analyte variables are prepared to predetermined values such that variance of the experimental samples is to statistically controlled.

8. The method of claim 1, wherein the spectral preprocessing includes a series of optimizations adapted to discern an optimal preprocessing algorithm for the fermentation process.

9. The method of claim 1, wherein the correlative model is generated using a univariate modeling methodology.

10. The method of claim 1, wherein the correlative model is generated using a multivariate modeling methodology.

11. The method of claim 1, the method further comprising iteratively refining the correlative model using modeling statistics such that correlation of the training data set to the offline measurements is increased.

12. The method of claim 1, the method further comprising generating a signal, alarm or report when the value of the target analyte deviates from a desired range based on a threshold limit.

13. The method of claim 1, wherein the target analyte includes at least one of ethanol concentration, fructose concentration, glucose concentration, degrees Brix value, NOPA value, pH value, ammonia concentration, tartaric acid concentration, malic acid concentration, total acidity value, citric acid concentration, acetic acid concentration, gluconic acid concentration, lactic acid concentration, glycerol concentration, sulfur dioxide concentration and polyphenolic content value.

14. A computer program product comprising a non-transitory machine-readable storage medium encoding instructions that, when executed by one or more programmable processors, cause the one or more programmable processors to perform operations comprising:
acquiring online Raman spectra of a fermentation process within a fermenter vessel at different times during the fermentation process to generate a training data set;
applying spectral preprocessing to the training data set such that non-correlative and covariant changes due to non-relevant species and/or properties are minimized and correlative changes due to a target analyte is amplified;

generating a correlative model of the target analyte such that spectral changes of the target analyte properties and/or compositions in the training data set corelate with offline assay measurements of physical samples taken from the fermentation process near in time to the acquired Raman spectra;

acquiring a subsequent online Raman spectrum during a subsequent run of the fermentation process within the fermenter vessel; and applying the correlative model to the subsequent online Raman spectrum to qualitatively and/or quantitatively predict a value of a property and/or composition of the target analyte.

15. The computer program product of claim 14, wherein the operations further comprise generating a signal, alarm or report when the value of the target analyte deviates from a desired range based on a threshold limit.

16. The computer program product of claim 14, wherein the target analyte includes at least one of ethanol concentration, fructose concentration, glucose concentration, degrees Brix value, NOPA value, pH value, ammonia concentration, tartaric acid concentration, malic acid concentration, total acidity value, citric acid concentration, acetic acid concentration, gluconic acid concentration, lactic acid concentration, glycerol concentration, sulfur dioxide concentration and polyphenolic content value.

17. A Raman analysis system, the system comprising:
a light source configured to emit excitation light;
an optical probe coupled to the light source via an optical cable such that the excitation light is emitted from a probehead of the probe into a sample volume, wherein the probe is configured to receive and transmit a Raman signal from the sample volume via the optical cable or another optical cable;
a spectrograph configured to spectrally separate the transmitted Raman signal;
a detector configured to receive the separated Raman signal and convert the separated Raman signal into a Raman spectrum; and
a controller configured to:
acquire online Raman spectra of a fermentation process within a fermenter vessel at different times during the fermentation process by actuating the light source to emit the excitation light and receiving the Raman spectrum from the detector;
apply a correlative model to the Raman spectrum to qualitatively and/or quantitatively predict a value of a property and/or composition of a target analyte, wherein the correlative model is adapted such that spectral changes of the target analyte properties and/or compositions in previously acquired Raman spectra correlate with offline assay measurements of physical samples taken from a previous fermentation process; and
monitor the fermentation process by periodically acquiring subsequent online Raman spectra.

18. The system of claim 17, wherein the controller is further configured to generate a signal, alarm or report when the value of the target analyte deviates from a desired range based on a threshold limit.

19. The method of claim 17, wherein the target analyte includes at least one of ethanol concentration, fructose concentration, glucose concentration, degrees Brix value, NOPA value, pH value, ammonia concentration, tartaric acid concentration, malic acid concentration, total acidity value, citric acid concentration, acetic acid concentration, gluconic acid concentration, lactic acid concentration, glycerol concentration, sulfur dioxide concentration and polyphenolic content value.

* * * * *